US010247676B1

(12) United States Patent
Shaw

(10) Patent No.: US 10,247,676 B1
(45) Date of Patent: Apr. 2, 2019

(54) OPTICAL MICRORESONATOR DEVICE WITH THERMAL ISOLATION

(71) Applicant: National Technology & Engineering Solutions of Sandia, LLC, Albuquerque, NM (US)

(72) Inventor: Michael J. Shaw, Tijeras, NM (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 96 days.

(21) Appl. No.: 15/661,725

(22) Filed: Jul. 27, 2017

Related U.S. Application Data

(63) Continuation-in-part of application No. 15/186,020, filed on Jun. 17, 2016, now abandoned.

(51) Int. Cl.
| | | |
|---|---|---|
| *G01N 21/77* | (2006.01) | |
| *G02B 6/02* | (2006.01) | |
| *G02B 6/293* | (2006.01) | |
| *G02B 6/024* | (2006.01) | |
| *G02B 6/12* | (2006.01) | |
| *G01J 5/44* | (2006.01) | |
| *G01J 5/08* | (2006.01) | |
| *G01N 21/68* | (2006.01) | |

(52) U.S. Cl.
CPC ........ *G01N 21/7746* (2013.01); *G01J 5/0821* (2013.01); *G01J 5/44* (2013.01); *G01N 21/68* (2013.01); *G02B 6/024* (2013.01); *G02B 6/02052* (2013.01); *G02B 6/02061* (2013.01); *G02B 6/12007* (2013.01); *G02B 6/293* (2013.01)

(58) Field of Classification Search
None
See application file for complete search history.

(56) References Cited

U.S. PATENT DOCUMENTS

| | | | | |
|---|---|---|---|---|
| 6,052,495 | A * | 4/2000 | Little | G02F 1/011 385/2 |
| 7,664,156 | B2 * | 2/2010 | Yamazaki | H01S 5/0612 372/34 |
| 7,667,200 | B1 | 2/2010 | Watts et al. | |
| 7,820,970 | B1 | 10/2010 | Shaw et al. | |
| 7,941,014 | B1 * | 5/2011 | Watts | B82Y 20/00 385/2 |

(Continued)

*Primary Examiner* — Sung H Pak
(74) *Attorney, Agent, or Firm* — Martin I. Finston; Capitol Patent & Trademark Law Firm; Wendy W. Koba

(57) ABSTRACT

A thermal microring optical sensor is configured such that a portion of the optical resonator and its associated waveguide are encased within a cladding structure to minimize scattering losses along the waveguide and also provide improved evanescent coupling efficiency between the waveguide and the resonator. Functioning as a thermal sensor, incoming radiation modifies the temperature of the resonator, which changes its resonant frequency and, as a result, the percentage of light that it evanescently couples from the waveguide. The cladding structure also functions as a mechanical support for the resonator disk, eliminating the need for a pedestal to suspend the disk above the support substrate. Thermally-induced buckling of the optical waveguide is also reduced by encasing the susceptible portion of the waveguiding within the cladding structure.

11 Claims, 8 Drawing Sheets

(56) References Cited

U.S. PATENT DOCUMENTS

| | | | | |
|---|---|---|---|---|
| 8,045,834 B2* | 10/2011 | Painter | ................... | B82Y 20/00 |
| | | | | 385/129 |
| 9,261,716 B2* | 2/2016 | Akiyama | ............... | G02F 1/0147 |
| 2005/0163185 A1* | 7/2005 | Vahala | ............... | G02B 6/29341 |
| | | | | 372/67 |
| 2006/0078254 A1* | 4/2006 | Djordjev | ............ | G02B 6/12007 |
| | | | | 385/32 |

\* cited by examiner

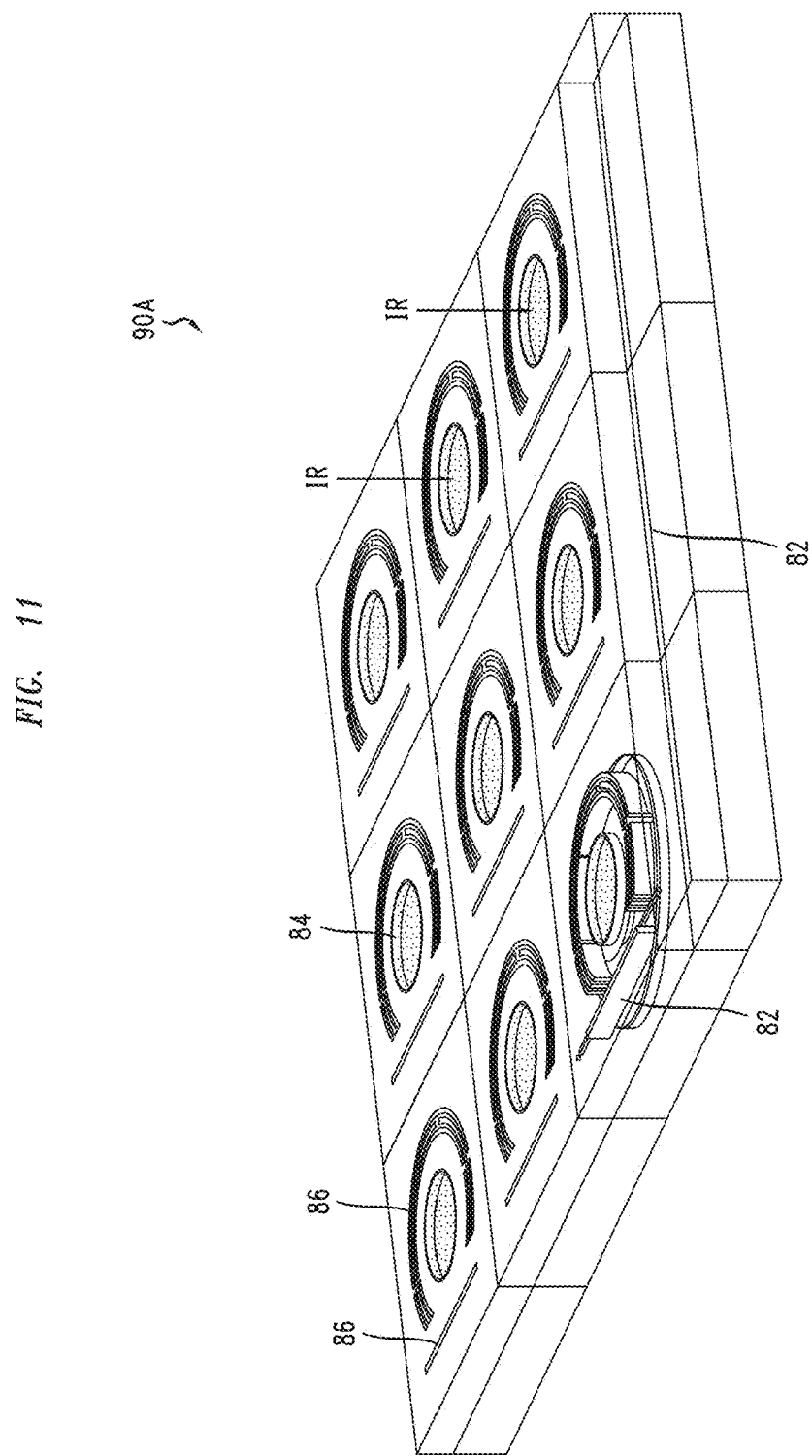

OPTICAL MICRORESONATOR DEVICE WITH THERMAL ISOLATION

CROSS-REFERENCE TO RELATED APPLICATIONS

This application is a continuation-in-part of U.S. application Ser. No. 15/186,020, filed Jun. 17, 2016 and herein incorporated by reference.

STATEMENT OF GOVERNMENT INTEREST

This invention was developed under Contract DE-AC04-94AL85000 between Sandia Corporation and the U.S. Department of Energy and under Contract DE-NA0003525 awarded to National Technology & Engineering Solutions of Sandia, LLC by the United States Department of Energy/National Nuclear Security Administration. The U.S. Government has certain rights in this invention.

BACKGROUND

Optical microring-resonator-based thermal sensors have previously been developed and used. The sensors are based on the thermo-optic effect and are fabricated in a manner to be thermally isolated from an underlying silicon wafer substrate so as to maximize the temperature excursion experienced by a sensor for a given amount of incident radiation. The thermal and physical isolation also minimize the impact of thermal phonon noise on the operation of the sensor.

The high quality factors (Q) that have been demonstrated in optical microring resonators have enabled the design and demonstration of highly sensitive microring-resonator-based sensors. For example, thermal sensors consist of a waveguide resonant microring structure, which is evanescently coupled to a bus waveguide. The microring itself is formed to be thermally insulated from the substrate upon which it is positioned.

One particularly useful configuration of such sensors is in a two-dimensional array topology, referred to as a "thermal microphotonic focal plane array" (TMFPA). While promising for many purposes, optical losses along the bus waveguides of a TMFPA are expected to degrade the performance of relatively large-sized arrays.

SUMMARY

One aspect of the present invention relates to a thermal microring optical sensor where a portion of the optical resonator and its associated bus waveguide are encased to minimize scattering losses along the waveguide and also provide improved evanescent coupling efficiency between the waveguide and the resonator. Functioning as a thermal sensor, incoming radiation modifies the temperature of the resonator, which changes its resonant frequency and, as a result, the percentage of light that it evanescently couples from the waveguide.

In another aspect of the invention, a plurality of sensors are formed as an array within a common substrate, where the use of encased regions including portions both the waveguide and resonator allow for larger-sized arrays to be formed, since scattering losses are significantly reduced when compared to prior art configurations.

A specific embodiment of the present invention takes the form of thermal microphotonic sensor for detecting infrared radiation comprising an optical resonator suspended above a substrate (the optical resonator having a resonant frequency which changes in response to heating of the optical resonator by the infrared radiation), an optical waveguide located proximate to the optical resonator to couple light from the optical waveguide into the optical resonator (and to transmit a remainder of the light not coupled into the optical resonator through the optical waveguide), a cladding structure disposed to surround and encase a section of the optical waveguide located proximate to the optical resonator and an adjacent portion of the optical resonator (the cladding structure formed of a material having a refractive index greater than 1.0), and a photodetector disposed at an output of the optical waveguide to receive the remainder of the transmitted light and generate therefrom an electrical output signal that is proportion to an intensity of detected infrared radiation.

Another embodiment of the present invention relates to a method of forming a thermal microphotonic sensor, including the steps of: providing a substrate; forming a first isolation layer over an exposed top major surface of the substrate; depositing a layer of sacrificial material over the first isolation layer, and patterning the layer of sacrificial material to define a boundary of a resonator air gap; forming a second isolation layer over the patterned layer of sacrificial material; depositing a layer of device material over the second isolation layer, and patterning the layer of device material to define an optical waveguide and an optical resonator disposed proximate to the optical waveguide so as to evanescently couple light therefrom; depositing a third isolation layer over the patterned device layer so as to encase a portion of the optical waveguide and an adjacent portion of the optical resonator, forming a cladding structure; creating openings through the third and second isolation layers to the layer of sacrificial material; preferentially etching the sacrificial material with respect to the second and third isolation layers, where the removal of the sacrificial material creates the air gap for the sensor structure; and exposing a central portion of the optical resonator such that incoming infrared radiation impinges a surface of the optical resonator and modifies the temperature thereof.

Other and further embodiments and aspects of the present invention will become apparent during the course of the following discussion and by reference to the accompanying drawings.

BRIEF DESCRIPTION OF THE DRAWINGS

One or more embodiments are illustrated by way of example, and not by limitation, in the figures of the accompanying drawings, wherein elements having the same reference numeral designations represent like elements throughout. It is emphasized that, in accordance with standard practice in the industry, various features may not be drawn to scale and are used for illustration purposes only. In fact, the dimensions of the various features in the drawings may be arbitrarily increased or reduced for clarify of discussion.

FIG. 11 is an isometric view of an array of thermal microphotonic sensors formed in accordance with one or more embodiments of the present invention.

DETAILED DESCRIPTION

Prior to describing the specific aspects of the present invention, a brief discussion of the principles associate with thermal microphotonic sensors is considered useful.

Figure 1:
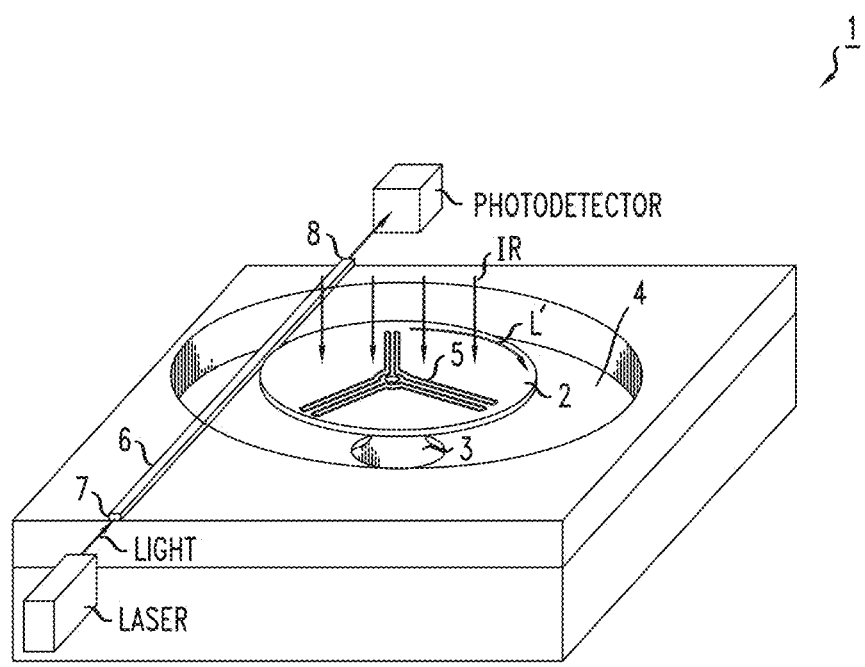
FIG. 1 shows a conventional thermal microphotonic sensor.

FIG. 1 shows a conventional thermal microphotonic sensor 1, comprising an optical resonator 2 (also referred to at times as an optical cavity, a microcavity, or a microring resonator) and an optical waveguide 6 disposed tangential to resonator 2. Optical resonator 2 is suspended on a support post 3 above a substrate 4 by a plurality of tethers 5 that are connected between optical resonator 2 and support post 3. This suspended configuration allows for resonator 2 to be thermally isolated from substrate 4 and, therefore, more sensitive to changes in ambient temperature. Optical waveguide 6 is located near a periphery of optical resonator 2 to allow an evanescent coupling of light between optical waveguide 6 and optical resonator 2.

As shown in FIG. 1, the incoming light can be provided by an external laser, which can be, for example, a single-frequency semiconductor laser such as a distributed Bragg reflector (DBR) laser operating at a wavelength of about 1.5 µm. The light from the laser is coupled into optical waveguide 6 at an input end 7 thereof and propagates along optical waveguide 6 to an output end 8, where the exiting light is detected by a photodetector.

In the example of FIG. 1, the light propagating along optical waveguide 6 will be evanescently coupled into optical resonator 2 when a frequency $f_L$ of the light (which is inversely proportional to its wavelength), is near a resonant frequency $f_0$ of optical resonator 2. Optical resonator 2 in the example of FIG. 1 is a ring resonator (also termed a microring resonator) in which a portion L' of the light propagating along optical waveguide 6 is evanescently coupled into resonator 2. The evanescently-coupled portion L' circulates around the periphery of resonator 2, as illustrated by the curved arrow in FIG. 1. The term "ring resonator" as used herein is intended to include optical resonators having a circular shape as shown in the example of FIG. 1 or having a polygonal shape (e.g. a square or rectangular shape), an elliptical shape, or an oval shape having curved or straight sides (the last also termed a racetrack shape).

Those skilled in the art will further understand that, although the portion L' is shown as circulating in a clockwise direction, the portion L' could circulate in a counterclockwise direction if optical waveguide 6 were located on an opposite side of resonator 2, or if the light in waveguide 6 were to propagate in a direction opposite to that shown in FIG. 1.

Figure 2:
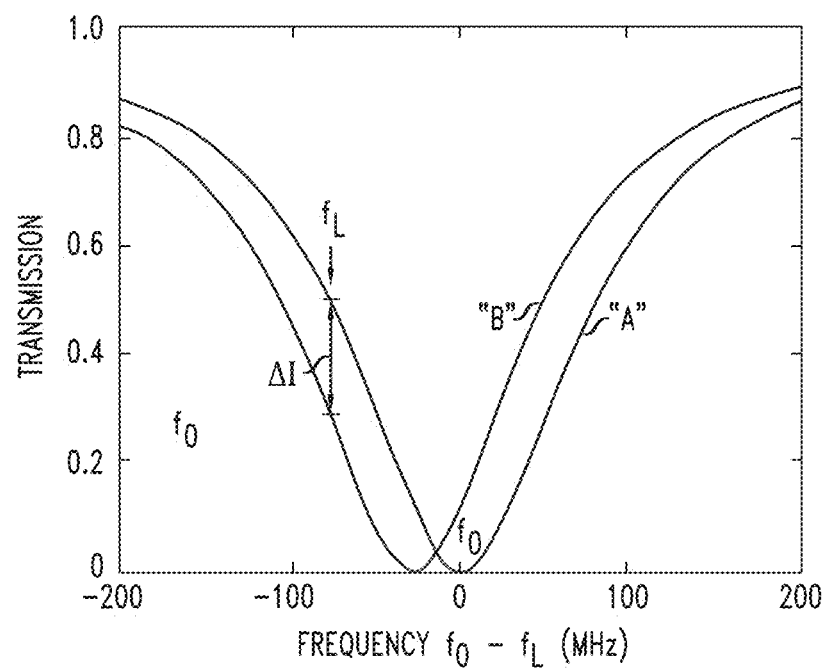
FIG. 2 is a graph of optical transmission as a function of frequency.

The coupling of the light between optical waveguide 6 and optical resonator 2 will depend upon the exact frequency $f_L$ of the light propagating along optical waveguide 6 relative to the resonant frequency $f_0$ of optical resonator 2. This can be understood with reference to FIG. 2. In FIG. 2, as the frequency $f_L$ of the light in optical waveguide 6 is varied about the resonant frequency $f_0$, a characteristic curve is generated for the light transmitted through optical waveguide 6 and detected with the photodetector. This characteristic curve, which is labeled "A" in FIG. 2, has an inverse Lorentzian shape with a full-width at half maximum (FWHM) which depends upon a quality factor Q of optical resonator 2. When the frequency $f_L$ of the light in optical waveguide 6 is tuned to coincide with the resonant frequency $f_0$ of resonator 2, only a minimum amount of the light will be detected by the photodetector since substantially all of the light is being coupled into optical resonator 2. Detuning the frequency $f_L$ of the light away from the resonant frequency $f_0$ reduces the coupling between optical waveguide 6 and resonator 2, thereby increasing the amount of light detected by the photodetector, as shown in FIG. 2.

If the frequency $f_L$ of the light is fixed at a particular reference point on the characteristic curve labeled "A" in FIG. 2, then any change in the resonant frequency $f_0$ of optical resonator 2 due to changes in its temperature can be measured simply by monitoring the amount of the light exiting optical waveguide 6 (using the photodetector, for example). This can be seen, for example, with the frequency $f_L$ being set at a 50% transmission point on the characteristic curve "A" as indicated by the downward-pointing arrow in FIG. 2. Any change in the resonant frequency $f_0$ of optical resonator 2 shifts the characteristic curve "A" and results in changing the amount of light transmitted through waveguide 6 and detected by the photodetector.

The change in the resonant frequency $f_0$ can accordingly provide a measurement of temperature change due to, for example, direct heating of optical resonator 2 by incident infrared radiation (shown as the downward-directed arrows in FIG. 1).

Thermal microphotonic sensor 1 described thus far can be used to form individual sensors, or a one-dimensional (1-D) or even a two-dimensional (2-D) sensor array, which is formed to comprise a plurality of sensors 1 on a common substrate 4. Such sensor arrays have applications for infrared imaging without the need for cryogenic cooling, for example.

Figure 3:
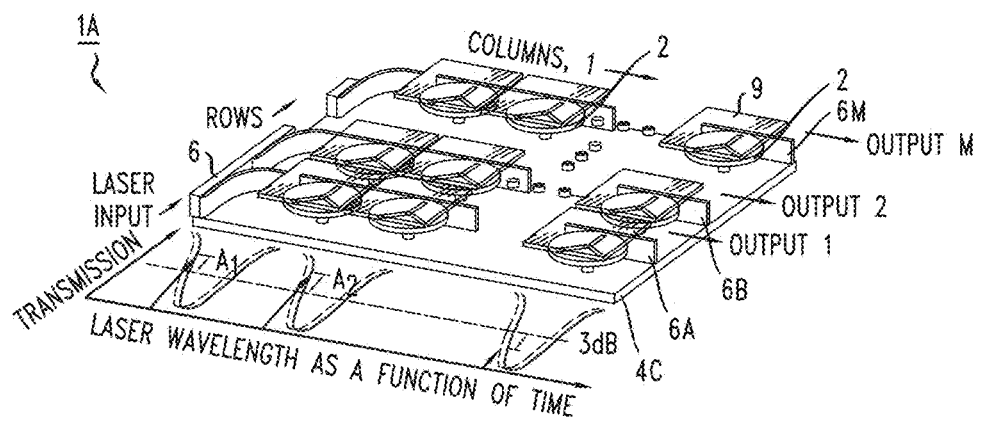
FIG. 3 is a simplified, isometric view of an example of a two-dimensional sensor array 1A including a plurality of optical resonators.

FIG. 3 is a simplified, isometric view of an example of a 2-D sensor array 1A including a plurality of optical resonators 2 located on a common substrate 4C, with resonators 2 arranged in rows and columns to form the 2-D sensor array 1A. An input waveguide 6 supplies the optical input signal. Each row of optical resonators 2 in FIG. 3 has its own optical waveguide, shown as waveguides 6A, 6B and 6M, which are all coupled to input waveguide 6 such that the incoming light beam is thereafter coupled into each bus waveguide 6A-6M so as to interact with each resonator disposed along each waveguide. Although only a few resonators 2 and waveguides 6 are shown in FIG. 3, one skilled in the art will understand that there can be up to one million or more optical resonators 2 on common substrate 4C when sensor array 1A forms a focal plane array (FPA) for imaging infrared radiation. Each optical resonator 2 can define a pixel in the focal plane array, with each pixel being, for example, 5-20 µm in size. In the example of FIG. 3, an infrared absorber (e.g. an infrared-absorbing coating 9 or an infrared-absorbing plate) can optionally be provided over each optical resonator 2. While not shown in this particular view, it is to be understood that a separate output photodetector is disposed at the exit of each of the bus waveguides 6A-6M and is used to measure the optical power eventually exiting the associated waveguide.

A major challenge in using arrays such as that shown in FIG. 3 is that when trying to incorporate a large number of devices into a large pixel sensor array, many ring resonators need to be interrogated in a row of devices, and only a single bus waveguide is associated with the row. It is expected that optical scattering (including both back-scattering and back-reflection) in the coupling regions where the individual resonators are interrogated will lead to accumulated waveguide losses that would be detrimental to the performance of the system. That is, the scattering results in significant attenuation of the propagating light by the time it reaches the end of each row.

Figure 4:
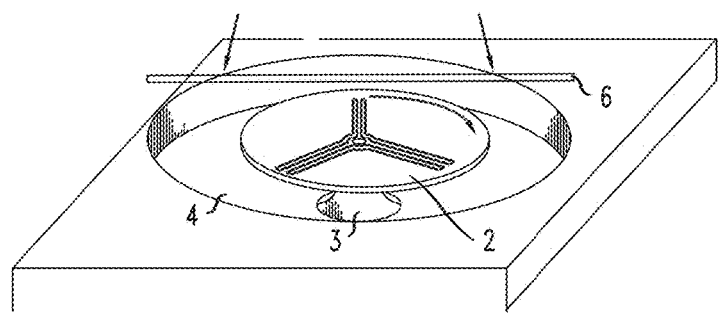
FIG. 4 is an isometric view of a typical thermal microphotonic sensor, illustrating regions where optical scattering occurs.

FIG. 4 is a photograph of a conventional sensor and waveguide of the kind also shown in FIGS. 1 and 3. It will be seen that in the coupling region, waveguide 6 crosses an air gap that is free of solid material, this gap being between optical resonator 2 and substrate 4. Near each end of the air gap, waveguide 6 experiences a change in the refractive index contrast between the waveguiding core and the surrounding material. This change in refractive index contrast causes optical scattering to occur.

The configuration of the present invention addresses problems associated with scattering from the waveguide (and thus attenuation of the propagating signal) by modifying the structure of a thermal microphotonic sensor in the region of the ring resonator. In particular, a cladding structure is added to the configuration and disposed to encase a portion of the waveguide and a portion of the resonator in the coupling region. The cladding material is selected to have a refractive index value that is relatively close to that of the waveguide and resonator (that is, the cladding material has a refractive index greater than the nominal value of $n=1$ defined for "air"). The provision of encasement by using this cladding material thus lessens the change in refractive index contrast (at times defined as $\Delta n$) experienced by light propagating in the waveguide (as discussed above with reference to FIG. 4). As a consequence, the inclusion of cladding material in accordance with one or more embodiments of the present invention can reduce scattering losses.

The cladding structure offers an additional benefit. As those skilled in the art will understand, the waveguide in the air gap region is a thin, elongated structure (again, see FIG. 4) having a significant coefficient of thermal expansion. As such, it is susceptible to buckling when the temperature changes. Buckling is undesirable inasmuch as it can lead to unwanted changes in the optical coupling between the waveguide and the resonator. Inasmuch as the structure is being utilized as a temperature sensor, it is expected that the waveguide will be subjected to changes in temperature, making buckling likely to occur in most applications. In accordance with the present invention, therefore, the mechanical support added by the inclusion of the cladding structure may at least partially suppress thermally-induced buckling.

Yet another benefit of utilizing a cladding structure encasement of portions of the waveguide and adjacent resonator in accordance with the present invention is that the evanescent field of the guided light within the waveguide extends farther within the cladding structure than it does within the air gap (by virtue of the difference of refractive index between the selected cladding material and air). As a result, the encased waveguide can be disposed further away from the resonator than prior art configurations and provide the same amount of optical coupling. This is advantageous because it relaxes the required fabrication tolerances.

As will be explained in more detail below, the cladding structure also provides mechanical coupling between the resonator and the substrate, thus eliminating the need to use a support post (or other structure) to suspend the resonator disk above the substrate (as is necessary in prior art configurations to provide thermal isolation between the resonator disk and the substrate).

Figure 5:
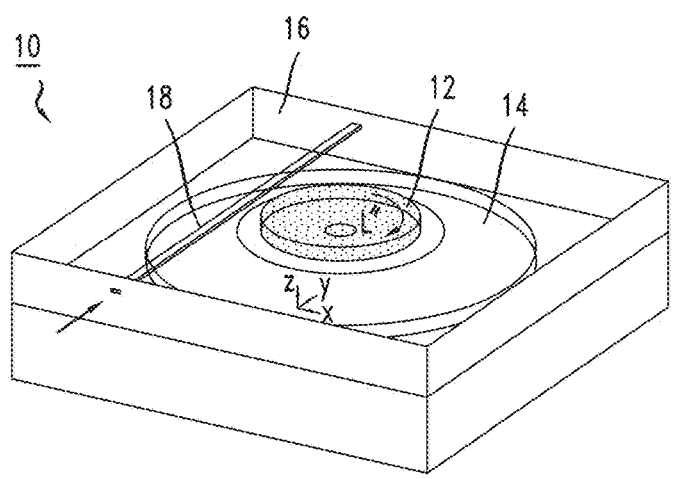
FIG. 5 is an isometric view of an exemplary encased sensor formed in accordance with one or more embodiments of the present invention.

FIG. 5 is an isometric view of an exemplary encased sensor 10 formed in accordance with the present invention. As shown, sensor 10 comprises an optical resonator 12 (also referred to as an optical cavity, a microcavity, or a microring resonator). As will be described in detail below, optical resonator 12 is suspended above a substrate 14 by an encasing cladding structure 16. Encasing cladding structure 16 is formed to enclose a portion of optical resonator 12 as well as a section of an optical waveguide 18 adjacent to optical resonator 12. This encased configuration allows for scattering losses from optical waveguide 18 to be significantly reduced, and it also serves to maintain resonator 12 in a suspended position with respect to substrate 14 without requiring a pedestal. It is to be understood that the cladding structure surrounds only a portion of resonator 12, allowing the remainder of the resonator surface 12S to remain exposed to the impinging radiation that is to be detected.

It should be noted that various embodiments of the present invention still retain an air gap between resonator 12 and substrate 14, although the gap will be somewhat less in some places than the prior art configurations using a resonator on a pedestal. The air gap is desirable for thermal isolation of resonator 12 from substrate 14, providing improved sensitivity of resonator 12 to changes in temperature.

For reasons explained above, cladding structure 16 can improve the evanescent coupling between optical waveguide 18 and optical resonator 12. Cladding structure 16 can also substantially reduce the scattering losses along waveguide 18 that are a result of the air gap interface between waveguide 18 and resonator 12.

Importantly, the material selected to form encasing cladding structure 16 should have a refractive index with a value suitable to better match that of waveguide 18 and resonator 12, so as to provide the improvements described herein. Air is defined to have a refractive index value of "$n=1$", and the common material (silicon nitride, $Si_3N_4$) used to form waveguide 18 and resonator 12 has a refractive index value (defined as "n") of about $n=2.0$ at a common wavelength of interest (1.5 µm). Silicon dioxide ($SiO_2$) is one exemplary material that is suitable for use as cladding structure 16, which has a refractive index value of about $n=1.44$ at a wavelength of 1.5 µm, thus creating a smaller $\Delta n$ than the default prior art air gap configuration. Other materials including, without limitation, silicon oxynitride, aluminum oxide, various spinnable polymers and various photoresists all have refractive index values greater than 1.0, and may be used to suit a particular purpose or address a specific need.

Similar to the example of FIG. 1, sensor 10 as shown in FIG. 5 functions by allowing the light propagating along optical waveguide 18 to be evanescently coupled into optical resonator 12 when a frequency $f_L$ of the light (which is inversely proportional to its wavelength), is near a resonant frequency $f_0$ of optical resonator 12. Cladding structure 16 minimizes scattering losses during this coupling, allowing for the optical coupling efficiency of sensor 10 to be greater than that of prior art (air gap) sensors. Again, optical resonator 12 in the example of FIG. 5 is a ring resonator (also termed a microring resonator) in which a portion L" of the light propagating along optical waveguide 18 is evanescently coupled into resonator 12. The evanescently-coupled portion L" circulates around the periphery of resonator 12, as illustrated by the curved arrow in FIG. 5. The term "ring resonator" as used herein is intended to include optical resonators having a circular shape as shown in the example of FIG. 5 or having a polygonal shape (e.g. a square or rectangular shape), an elliptical shape, or oval shape (also termed a racetrack shape). Those skilled in the art will further understand that, although the portion L' is shown as circulating in a clockwise direction, the portion L" could circulate in a counterclockwise direction if optical waveguide 18 were located on an opposite side of resonator 12, or if the light in waveguide 18 were to propagate in a direction opposite to that shown in FIG. 5.

Figure 6:
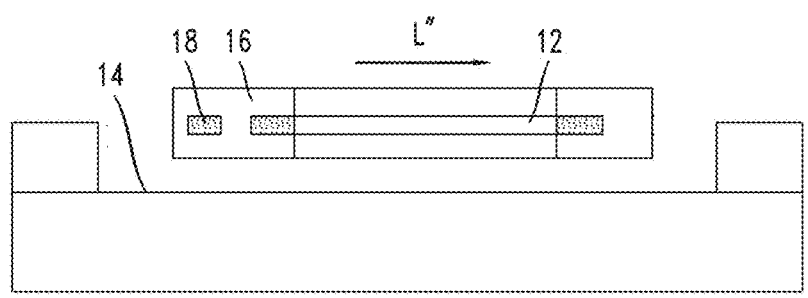
FIG. 6 is a side view of the sensor of FIG. 5, taken along line 6-6.
Figure 7:
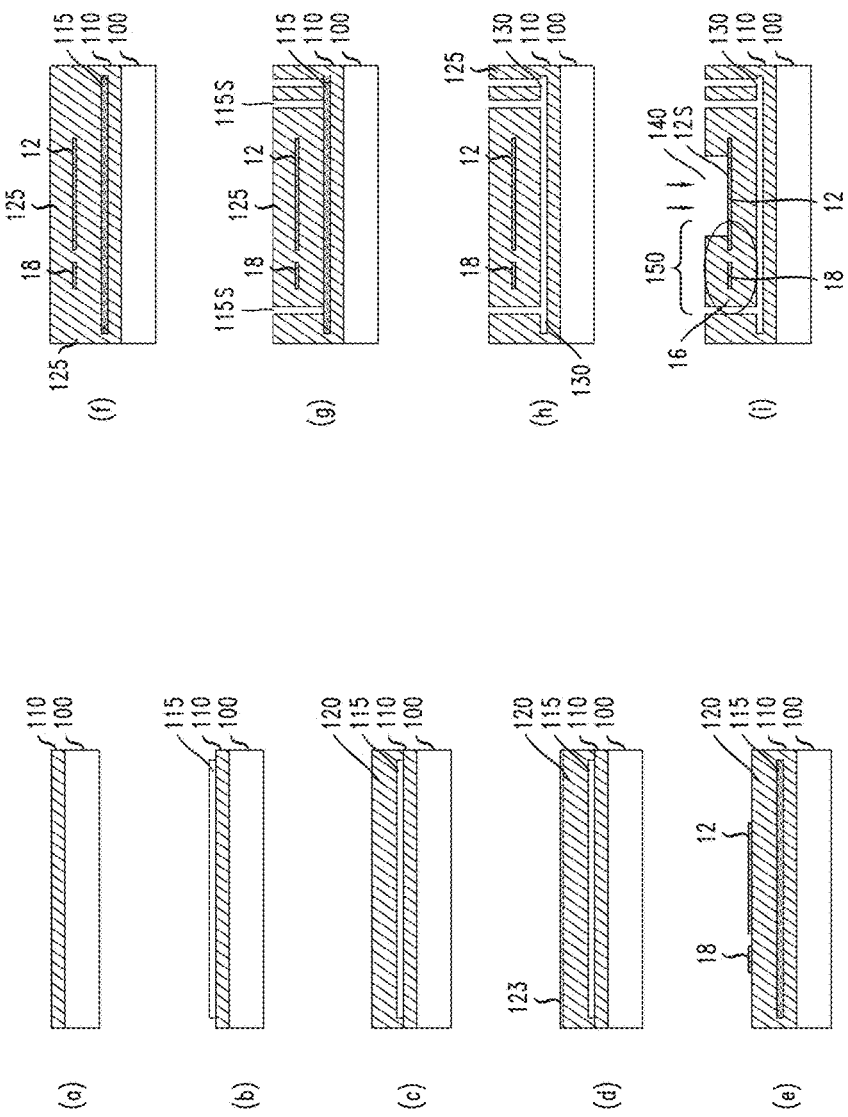
FIG. 7 contains a set of diagrams illustrating an exemplary process of fabricating an encased sensor formed in accordance with one or more embodiments of the present invention.

FIG. 6 is a side view of sensor 10, taken along line 6-6 of FIG. 5. The view of FIG. 6 clearly shows cladding structure 16 encasing portions of optical waveguide 18 and optical resonator 12. This view also clearly shows the ability of cladding structure 16 to provide the mechanical strength necessary to suspend resonator 12 about substrate 14, while also providing the air gap between substrate 14 and resonator 12 that is useful to improve thermal isolation of resonator 12. Cladding structure 16, by providing a closer match to the refractive index value of waveguide 18 and resonator 12, reduces scattering losses and improves the evanescent coupling of a beam propagating at the resonant wavelength of resonator 12. Moreover, inasmuch as cladding structure 16 is formed to extend between the "edges" of the gap (see FIG. 4), waveguide 18 remains encased along this path and is therefore less likely to experience buckling Advantageously, providing an encasing cladding structure with a thermal microphotonic sensor in accordance with the present invention may easily be accommodated within a conventional sensor fabrication process. FIG. 7 illustrates an exemplary process of forming a thermally isolated, encased optical microring resonator-based thermal sensor in accordance with one or more embodiments of the present invention. Referring to FIG. 7(a), the process begins by depositing an oxide layer 110 on a substrate 100. Following this step, a sacrificial layer 115 is disposed over a portion of oxide 110, as shown in FIG. 7(b). The extent of sacrificial layer 115 is related to the extent of opening 20 that will ultimately be formed underneath resonator 12. Sacrificial layer 115 is preferably formed of a polysilicon material having a thickness in the range of 1-20 µm. While not evident in this view, sacrificial layer 115 may be patterned to take the desired shape of the bottom of the cavity over which the resonator will be suspended (e.g., a "circular" opening, as shown in the photograph of FIG. 4, and illustrated in FIGS. 1 and 5).

Following the formation of sacrificial layer 115, a second oxide layer 120 is then deposited, as shown in FIG. 7(c), so that sacrificial layer 115 is completely surrounded by oxide material. At this point, a relatively thin layer of material used to form waveguide 18 and 20 (defined as "device layer 123") is deposited on the exposed surface of oxide layer 120, as shown in FIG. 7(d). Device layer 123 typically comprises a layer of silicon nitride ($Si_3N_4$), and may be formed using a Low Pressure Chemical Vapor Deposition (LPCVD) process or a Plasma Enhanced Chemical Vapor Deposition (PECVD) process. The structure of FIG. 7(d) is then patterned, using well-known techniques, to form both waveguide 18 and resonator 12. FIG. 7(e) illustrates the structure at this point in the process. In particular, device layer 123 is patterned and etched to form waveguide 18, resonator 12, and selected release holes (not shown). The release holes provide access to sacrificial layer 115 so as to allow for the ultimate removal of this layer from the final form of the structure. The specific topology of resonator 12 may be configured, as will be discussed below in association with FIG. 9 to include one or more expansion slots to relieve any residual stress.

An encasing oxide layer 125 is then grown (or deposited) over the exposed surface of the structure, resulting in the configuration as shown in FIG. 7(f). As a result of this step, the combination of waveguide 18 and resonator 12 is fully encased. Thus, any optical signal propagating along waveguide 18 that is evanescently coupled into resonator 12 will exhibit little or no scattering (as a function of the refractive index of the material used to form resonator 12 and oxide layers 110 and 125). The combination of oxide layers 110 and 125 in the vicinity of waveguide 18 and resonator 12 defining encasing structure 16. Turning to FIG. 7(g), encasing oxide layer 125 is shown as being patterned, and then etched to expose top surface regions 115S of sacrificial layer 115. Once exposed, an etchant that preferentially removes the material of sacrificial layer 115 with respect to the oxides forming layers 120 and 125, is used to remove sacrificial layer 115 to form the structure as shown in FIG. 7(h). It is clearly shown in FIG. 7(h) that thermal isolation space 130 is created by virtue of removing sacrificial layer 115 from the structure.

A final step in the formation of the structure is shown in FIG. 7(i), where again oxide layer 125 is patterned and etched to remove a central portion 140 of layer 125 and expose top surface 12S of resonator 12. In accordance with the described operation of such a resonator, it is necessary for the device to be exposed so that it is receptive to IR radiation and performs as a temperature-dependent device. As shown, by removing only central portion 140 of oxide layer 125, waveguide 18 and an adjacent portion of resonator 12 remain encased (defined as encased structure 16 and particularly shown in FIG. 6), thereby maintaining the high coupling efficiency between waveguide 18 and resonator 12.

Figure 8:
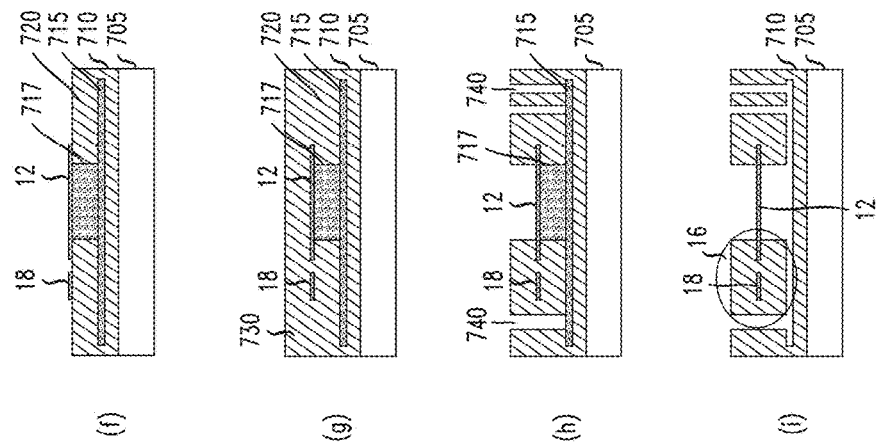
FIG. 8 contains a set of diagrams illustrating an alternative exemplary process of fabricating an encased sensor formed in accordance with one or more embodiments of the present invention.
Figure 8:
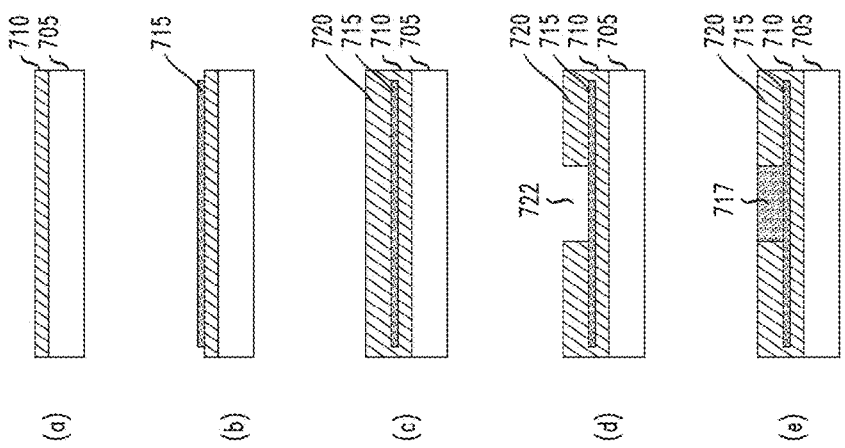

FIG. 8 illustrates an alternative process also suitable for forming the encased sensor structure of the present invention. Similar to the process described above, the process begins by forming an oxide surface layer 710 over a silicon substrate 700. This is shown in FIG. 8(a). Also, similar to the above-described process, the next step in the process shown in FIG. 8 is the formation of a sacrificial layer 715 over a portion of oxide layer 710 (FIG. 8(b)). As before, the extent of sacrificial layer 715 defines the extent of the isolation region ultimately formed underneath resonator 12. A second oxide layer 720 is then formed to cover sacrificial layer 715 in the manner shown in FIG. 8(c).

In accordance with this embodiment of the present invention, the next step is the removal of a central portion of second oxide layer 720. Various techniques can be used to pattern and etch second oxide layer 720 to remove the desired amount of the central region, shown as region 722 in FIG. 8(d). Following that step, a layer of sacrificial material 717 is deposited in region 722, and the structure is planarized to form the configuration as shown in FIG. 8(e).

Then similar to the process described above, the silicon nitride material for waveguide 18 and resonator 12 is deposited, patterned and etched to form the specific structure of waveguide 18 and resonator 12 as shown in FIG. 8(*f*). Subsequent to this step, the structure is then covered by a third oxide layer 730, as shown in FIG. 8(*g*), where the combination of layers 720 and 730 will ultimately form encasing cladding structure 16 for waveguide 18 and resonator 12.

In the following two process steps, sacrificial layers 715 and 717 are removed to form the final structure. First, as shown in FIG. 8(*h*), trenches 740 are formed through third oxide layer 730, exposing portions of sacrificial layer 715. In accordance with this embodiment of the present invention, the patterning used in this step also removes a portion of layer 730 overlying resonator 12, exposing a central portion of resonator 12 (as required for operation as a thermal sensor).

A suitable etchant is then used that removes all of sacrificial layers 715 and 717, forming the final structure as shown in FIG. 8(*i*). Again, the patterning and etching steps may be used to form additional stress relief slots and thermal isolation regions through oxide layer 730.

Figure 9:
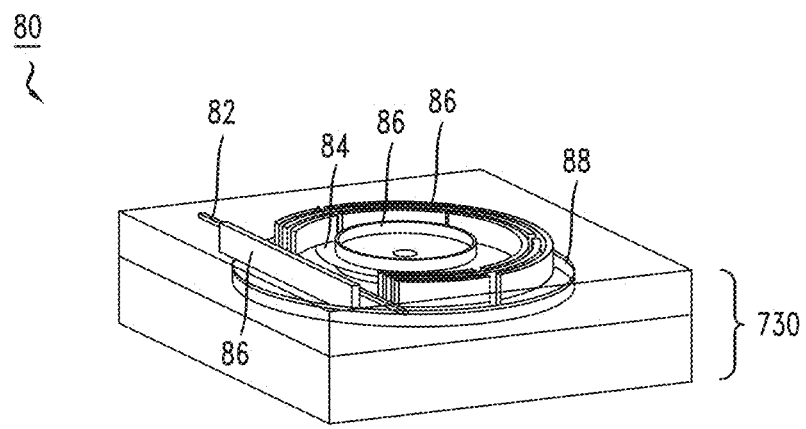
FIG. 9 is an isometric view of an exemplary thermal microphotonic sensor formed in accordance with one or more embodiments of the present invention to include a plurality of thermal expansion slots.

For relief against mechanical stress due to thermal expansion and contraction, it is desirable to provide expansion slots that penetrate the oxide layer that suspends the resonator (e.g., oxide layer 120 of FIG. 7, oxide layer 720 of FIG. 8). FIG. 9 illustrates a perspective view of an encased microphotonic thermal sensor 80 formed in accordance with at least one embodiment of the present invention to include several expansion slots (the cladding structure being shown in phantom so that the internal elements can be seen). In particular, sensor 80 includes an optical waveguide 82 and associated optical resonator 84. Evident in this view is a set of expansion slots 86 formed in upper oxide layer (for example, third oxide layer 730 of FIG. 8), used to accommodate residual stress and provide thermal isolation for resonator 84, as well as provide access to releasing sacrificial material 88 below and in the vicinity of resonator 84. Resonator 84 includes an oxide undercut which, in various embodiments, provides more sensitivity due to the thermal isolation from the lower cladding and/or the substrate.

A further advantage of these slots is that they can contribute to the thermal isolation of the resonator with respect to the substrate (and other elements in the structure). That is, heat conducted away from a given resonator through the suspending oxide layer will not reach a neighboring resonator until a finite period of time has elapsed. Thermal crosstalk can be suppressed, for example, by making this time period longer than a measurement interval. This can be achieved, in one case, by providing a serpentine-like thermal path away from the resonator (as opposed to the simple straight line path).

Figure 10:
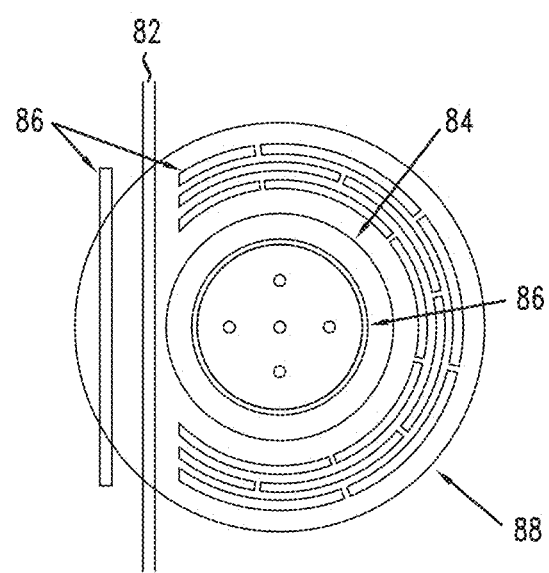
FIG. 10 is a diagrammatic illustration of a top surface of the exemplary sensor of FIG. 9.

FIG. 10 is a diagrammatic representation of a top view of sensor 80 of FIG. 9, illustrating an exemplary configuration of expansion slots 86 that have been laid out such that there will be a relatively tortuous thermal path between adjacent resonators. As shown, there are three rows of slots 86 laid out so that they overlap in the radial direction. As a consequence, conducted heat cannot propagate in a purely radial direction, but must instead follow a path that turns back on itself in a zigzag manner.

FIG. 11 illustrates an exemplary two-dimensional array 90A that may be formed using the techniques of the present invention to create encased sensors at each location where a bus waveguide comes within coupling proximity of an optical resonator. The particular array 90A comprises a plurality of sensors 80 as shown in FIG. 9, and disposed along various bus waveguides. The cladding structure has been removed from one of the sensors to better show the locations of the waveguide, resonator and slot locations. Also shown in this view is the exposed open region 92 of each resonator, which may be coated with a material that improves its thermal sensitivity.

Although the present disclosure and its advantages have been described in detail, it should be understood that various changes, substitutions and alterations can be made herein without departing from the spirit and scope of the disclosure as defined by the appended claims. Moreover, the scope of the present invention is not intended to be limited to the particular embodiments of the process, design, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A thermal microphotonic sensor for detecting infrared radiation, comprising:
    an optical resonator suspended above a substrate, the optical resonator having a resonant frequency which changes in response to heating of the optical resonator by the infrared radiation;
    an optical waveguide located proximate to the optical resonator to couple light from the optical waveguide into the optical resonator, and to transmit a remainder of the light not coupled into the optical resonator through the optical waveguide;
    a cladding structure formed of a material having a refractive index greater than 1.0; and
    a photodetector disposed at an output of the optical waveguide to receive the remainder of the transmitted light and generate therefrom an electrical output signal that is responsive to detected infrared radiation;
    wherein: the cladding structure is disposed to surround and encase a section of the optical waveguide located proximate to the optical resonator and an adjacent portion of the optical resonator, and the cladding structure is coupled to the substrate in a manner that suspends the optical resonator above the substrate.

2. The thermal microphotonic sensor as defined in claim 1, wherein the cladding structure is formed of a material that suppresses thermally-induced buckling of the optical waveguide.

3. The thermal microphotonic sensor as defined in claim 1, wherein the cladding structure is formed of a material that enhances optical coupling between the optical waveguide and the optical resonator.

4. The thermal microphotonic sensor as defined in claim 1, wherein the optical resonator and the optical waveguide are formed of silicon nitride, and the cladding structure is formed of a material selected from the group consisting of: silicon dioxide, silicon oxynitride, aluminum oxide, spinnable polymers and photoresists.

5. The thermal microphotonic sensor as defined in claim 1, wherein the cladding structure comprises silicon dioxide.

6. The thermal microphotonic sensor as defined in claim 1, wherein, the cladding structure is configured to include at least one vertical slot extending therethrough for providing relief from expansion and contraction during changes in temperature.

7. The thermal microphotonic sensor as defined in claim 6, wherein, the at least one vertical slot comprises a plurality of slots.

8. The thermal microphotonic sensor as defined in claim 7, wherein, the plurality of slots are disposed in a tortuous pattern across a top surface of the cladding structure to enhance thermal isolation of the sensor from adjacent elements.

9. A one-dimensional thermal microphotonic sensor array comprising:
   an optical waveguide disposed on a substrate;
   a plurality of separate optical resonators positioned along a length of the optical waveguide and suspended over the substrate, each optical resonator having a resonant frequency which changes in response to heating of the optical resonator from incident infrared radiation;
   a plurality of cladding structures associated with the plurality of separate optical resonators in a one-to-one relationship, each said cladding structure formed of a material having a refractive index greater than 1.0; and
   a photodetector disposed at an output of the optical waveguide to receive the remainder of the transmitted light and generate therefrom an electrical output signal that is responsive to detected infrared radiation;
   wherein: each said cladding structure is disposed to surround and encase a section of the optical waveguide located proximate to the associated optical resonator and an adjacent portion of the optical resonator, and each said cladding structure is coupled to the substrate in a manner that suspends the associated optical resonator above the substrate.

10. The one-dimensional thermal microphotonic sensor array of claim 9, wherein at least two optical resonators of the plurality of separate optical resonators have different resonant frequencies.

11. A two-dimensional thermal microphotontic sensor array, comprising:
   an input optical waveguide disposed on a substrate;
   a plurality of bus optical waveguides disposed along and coupled to the input optical waveguide;
   a separate plurality of optical resonators positioned along a length of each bus optical waveguide of the plurality of bus optical waveguides so as to form a two-dimensional array of optical resonators, each optical resonator suspended over the substrate and having a resonant frequency which changes in response to heating of the optical resonator from incident infrared radiation;
   a plurality of cladding structures associated with separate optical resonators of the two-dimensional array of optical resonators in a one-to-one relationship, each said cladding structure formed of a material having a refractive index greater than 1.0; and
   a plurality of photodetectors, each photodetector disposed at an output of an associated bus optical waveguide to receive the remainder of the light transmitted along the associated bus optical waveguide and generate therefrom an electrical output signal that is responsive to detected infrared radiation;
   wherein: each said cladding structure is disposed to surround and encase a section of the optical waveguide located proximate to the associated optical resonator and an adjacent portion of the optical resonator, and each said cladding structure is coupled to the substrate in a manner that suspends the associated optical resonator above the substrate.

* * * * *